United States Patent [19]

Ditchburn

[11] Patent Number: 4,501,555
[45] Date of Patent: Feb. 26, 1985

[54] PERIODONTAL PROBES

[75] Inventor: Frederick Ditchburn, Weybridge, England

[73] Assignee: Dentsply Research & Development Corp., Milford, Del.

[21] Appl. No.: 576,287

[22] Filed: Feb. 2, 1984

[30] Foreign Application Priority Data

Mar. 21, 1983 [GB] United Kingdom ............... 8307716

[51] Int. Cl.³ .......................... A61C 1/00; A61C 3/00
[52] U.S. Cl. ........................................ 433/29; 433/72
[58] Field of Search .................... 433/141, 72, 75, 32, 433/29

[56] References Cited

U.S. PATENT DOCUMENTS

| 2,949,107 | 8/1960 | Ziegler. | |
| 3,559,292 | 2/1971 | Weissman. | |
| 3,935,640 | 2/1976 | Cohan | 433/75 |
| 4,203,223 | 5/1980 | Lautenschlager. | |
| 4,375,964 | 3/1983 | Knopp et al. | 433/29 |

FOREIGN PATENT DOCUMENTS 2086232A 5/1982 United Kingdom.

Primary Examiner—Robert Peshock
Attorney, Agent, or Firm—C. Hercus Just

[57] ABSTRACT

A periodontal probe (3) comprises an elongate shaft terminating in a measuring tine (4) having a plurality of spaced transverse grooves (5) formed therein, the probe being formed of a material translucent to light. In use, the probe is mounted in a handle provided with a source of light (6) to direct light along the length of the probe whereby the grooves formed in the tine appear as comparatively brightly illuminated marks.

3 Claims, 1 Drawing Figure

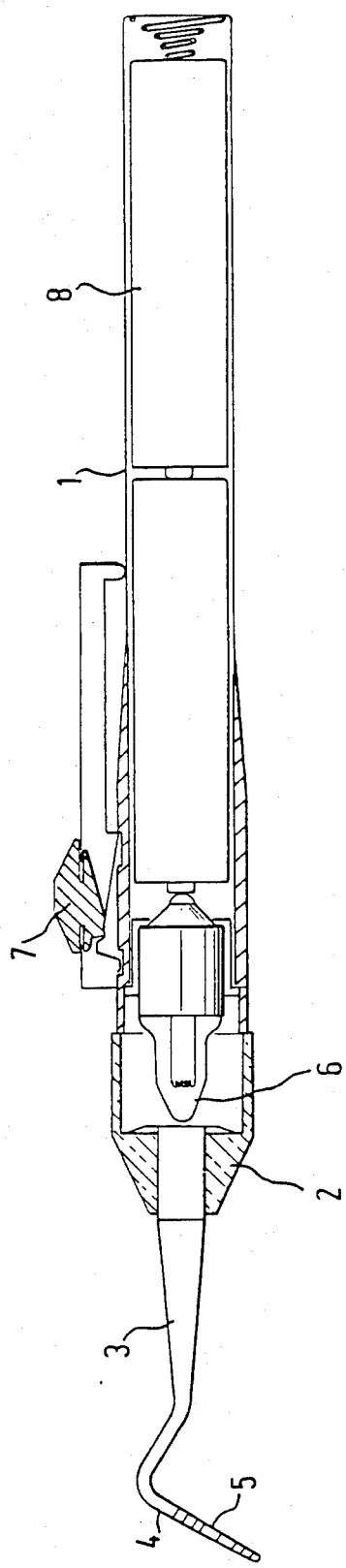

PERIODONTAL PROBES

BACKGROUND OF THE INVENTION

This invention is concerned with improvements in and relating to periodontal probes and apparatus incorporating such probes.

A periodontal probe is an instrument used in dentistry to measure the depths of pockets or recesses which form between the tooth and the gum when the patient is suffering from an oral disorder known as periodontoclasia. It also is employed in endodontic techniques involving measurements of root canals. In contrast to a conventional probe, the tine of a periodontal probe is marked at predetermined distances along its length, usually by means of grooves formed into the material of the tine, so that the user can, at least in theory, see how far the probe has penetrated a pocket, recess, or root canal, and thus determine its depth. A periodontal probe should be light in weight, as no excessive pressure should be applied to the floor or bottom of the pocket, recess, or root canal if accurate measurements are to be obtained, and its tip should be blunt, especially so that piercing of the soft floor or bottom of a pocket or recess is avoided.

Periodontal probes made of metal have been available for many years. The simplest form of periodontal probe is one, generally formed of stainless steel, having a round or flattened tine, the tine having a number of transverse grooves formed in it along its length. In practice, however, it is difficult to see the grooves to determine the depth of the pocket or recess because there is little effective difference in color between the grooves and the rest of the tine.

In order to overcome this problem, it has been proposed to fill the grooves with a material of contrasting color to the material of the tine. However, it has been found, in practice, that the rings of colored material tend to chip and/or wear during handling and repeated cycles of sterilization.

Examples of certain periodontal probes developed heretofore are disclosed in the following prior patents:

1. U.S. Pat. No. 3,559,292 to Weissman, dated Feb. 2, 1971, illustrates a dental guage including a flexible and extendable member operated by a slide on a handle movable relative to a scale on the handle.

2. U.S. Pat. No. 4,203,223 to Lautenschlager et. al., dated May 20, 1980, includes a scale-marked measuring shaft slidably carried by a sleeve on the head of the instrument and actuated by a collar movable along a threaded portion of an elongated handle to cause a leaf spring to project the measuring shaft into a gingival sulcus. The shaft has spaced scale markings therealong.

3. Published British Patent Application Ser. No. 2,086,232A discloses a dental probe having a conventional scale arrangement on the probe member.

4. Though not directed to a periodontal instrument, U.S. Pat. No. 2,949,107 to Ziegler, dated Aug. 16, 1960, pertains to a dental vitality instrument known as a pulp tester and includes a probe terminal for contacting a tooth to determine the vitality thereof by means of an electric current. The probe is supported within a casing extension of translucent material within which a small electric bulb is mounted and is illuminated by batteries within the handle of the instrument.

SUMMARY OF THE INVENTION

It is an object of the present invention to provide an improved periodontal probe in which, in use, the grooves are well contrasted with the body of the tine.

According to the invention, there is provided a periodontal probe comprising an elongate shaft terminating in a measuring tine having a plurality of spaced transverse grooves formed therein, and the probe is formed of a material translucent to light.

In use, the probe of the invention is mounted in a handle provided with a light source which directs light through the probe whereby the grooves formed in the tine appear as comparatively brightly illuminated marks against the background of the tine material.

The invention also provides a probe, as described above, mounted in a holder or handle provided with a light source.

BRIEF DESCRIPTION OF THE DRAWING

In order that the invention may be well understood, reference will now be made to the accompanying drawing in which the single FIGURE is a longitudinal section through a probe or holder assembly illustrating the invention.

DETAILED DESCRIPTION OF THE PREFERRED EMBODIMENT OF THE INVENTION

As shown in the drawing, a periodontal probe assembly in accordance with the invention comprises a probe handle comprising a body member 1 terminating, at one end thereof, in a probe-holding member 2 in which is detatchably mounted probe 3 which is formed of translucent material and the tine 4, of the probe being provided with a series of equally spaced transverse devices such as grooves 5. An electric light bulb 6 is mounted in body member 1 adjacent the inner end of probe 3 and is connected by a conventional circuit, including switch 7, to batteries 8 mounted in body member 1. Switch 7 is of conventional construction and when operated energizes bulb 6 so that light therefrom shines along the length of probe 3 thereby illuminating grooves 5 as rings or bands of light.

As noted above, probe 3 is formed of a material translucent to light, and thus, for example, may be formed of glass. For safety's sake, however, it is generally preferred that the probe be formed of a less brittle material, for example, of a translucent plastics material such as a homo- or copolymer of methyl methacrylate.

The holder or handle for holding the probe need not be provided with its own internal source of electricity, but may be appropriately connected to a suitable remote source of electricity, or illumination may be provided through fiber optic bundles illuminated by a suitable source.

As in conventional periodontal probes, the tine of the probe will generally be inclined at any angle to the axis of the supporting shaft which renders the instrument suitable for the purpose envisaged.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown therein.

It is claimed:

1. A self-contained periodontal probe and light source comprising, in combination, an elongated handle body containing a source of light, a light-transmitting probe shaft supported by one end of said handle body and terminating in a tapered light-transmitting measuring tine extending laterally from said shaft and provided with a series of spaced transverse devices thereon, said light source being adapted to illuminate said light probe and devices thereon to permit ready visual observation of said devices on said tine as rings of light when said probe is in use.

2. The periodontal probe according to claim 1 further characterized by said handle body being hollow and said source of light comprising an electric light bulb positioned within said handle body adjacent the end of said light-transmitting probe shaft nearest said handle and including electric battery means within said handle body, and a conventional electric circuit including a switch and connecting said electric light bulb and battery means.

3. The periodontal probe according to claim 1 in which said devices are transverse grooves spaced along said tine and appearing as bands of light when illuminated to facilitate use of said tine as a measuring probe to determine the depth of a pocket or recess in a dental environment.

* * * * *